US009561158B2

(12) United States Patent
Picha

(10) Patent No.: US 9,561,158 B2
(45) Date of Patent: Feb. 7, 2017

(54) BRIDLE CATHETER WITH ILLUMINATING END

(71) Applicant: Applied Medical Technology, Inc., Brecksville, OH (US)

(72) Inventor: George J. Picha, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 384 days.

(21) Appl. No.: 13/836,037

(22) Filed: Mar. 15, 2013

(65) Prior Publication Data

US 2014/0275805 A1  Sep. 18, 2014

(51) Int. Cl.
*A61B 1/06* (2006.01)
*A61J 15/00* (2006.01)
*A61M 25/01* (2006.01)

(52) U.S. Cl.
CPC ............ *A61J 15/0061* (2013.01); *A61B 90/30* (2016.02); *A61J 15/0003* (2013.01); *A61B 2090/309* (2016.02); *A61M 25/0127* (2013.01)

(58) Field of Classification Search
CPC ... A61B 1/0661; A61B 1/0684; A61B 5/0084; A61B 1/00096
USPC ................................ 600/101–249; 604/94.01
See application file for complete search history.

(56) References Cited

U.S. PATENT DOCUMENTS

| | | | |
|---|---|---|---|
| 4,778,448 A | 10/1988 | Meer | |
| 5,185,005 A | 2/1993 | Ballantyne | |
| 5,257,636 A | 11/1993 | White | |
| 5,819,727 A | 10/1998 | Linder | |
| 6,126,647 A * | 10/2000 | Posey | A61M 25/0127 600/12 |
| 6,631,715 B2 | 10/2003 | Kirn | |
| 7,534,228 B2 | 5/2009 | Williams | |
| 7,827,985 B2 | 11/2010 | Pastron | |
| 2005/0236001 A1 | 10/2005 | Williams | |
| 2006/0037617 A1 | 2/2006 | Walke et al. | |
| 2006/0081253 A1 | 4/2006 | Nelson | |
| 2006/0157059 A1 | 7/2006 | Johnson et al. | |
| 2006/0207604 A1 | 9/2006 | Nelson et al. | |

(Continued)

FOREIGN PATENT DOCUMENTS

WO  2014/109846 A1  7/2014

OTHER PUBLICATIONS

International Search Report of corresponding PCT Application No. PCT/US2014/023191; Dated Jul. 1, 2014.

(Continued)

*Primary Examiner* — Ellen C Hammond
*Assistant Examiner* — Christina Negrellirodrigue
(74) *Attorney, Agent, or Firm* — Pearne & Gordon LLP

(57) ABSTRACT

An illuminating bridle catheter installation system includes a flexible member having a leading end and a trailing end with a first magnet coupled to the leading end of the flexible member, and a retrieving member having a leading end and a trailing end with two non-contacting second magnets coupled to the leading end of the retrieving member. An illuminating member is coupled to one of the flexible member or the retrieving member and the illuminating member is coupled to an electronic circuit having a switch that allows the illuminating member to be illuminated when the first magnet meets the second magnets.

18 Claims, 5 Drawing Sheets

(56) References Cited

U.S. PATENT DOCUMENTS

| | | | |
|---|---|---|---|
| 2008/0114207 A1* | 5/2008 | Krupa | A61B 1/00068 |
| | | | 600/178 |
| 2010/0076269 A1 | 3/2010 | Makower et al. | |
| 2011/0004068 A1* | 1/2011 | Bruto Da Costa | 600/249 |
| 2012/0083658 A1* | 4/2012 | Hahn | A61B 1/32 |
| | | | 600/205 |
| 2012/0238830 A1* | 9/2012 | Vukeljic et al. | 600/249 |
| 2014/0196723 A1 | 7/2014 | Kirkpatrick et al. | |

OTHER PUBLICATIONS

Extended European Search Report for Corresponding Application No. EP 14 76 9475; Dated Sep. 14, 2016.

\* cited by examiner

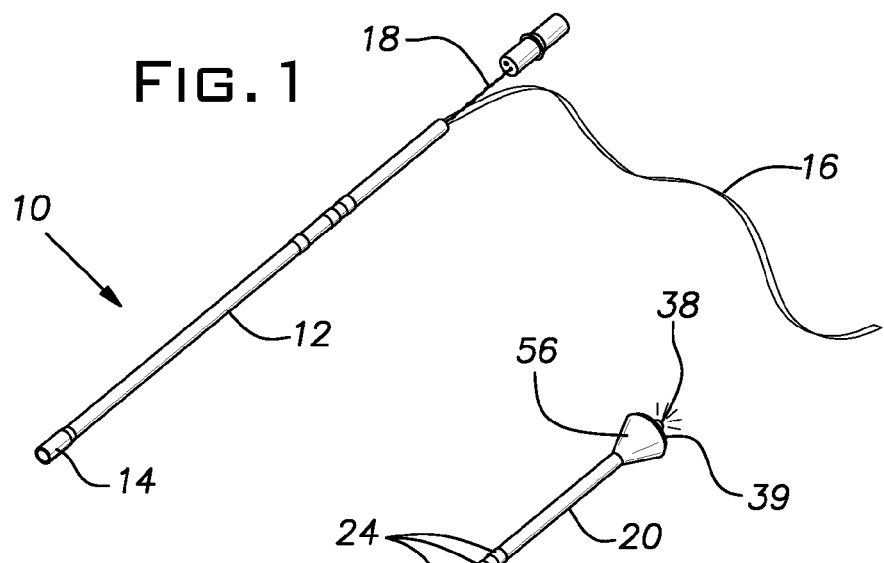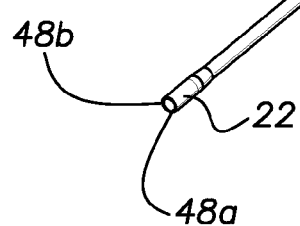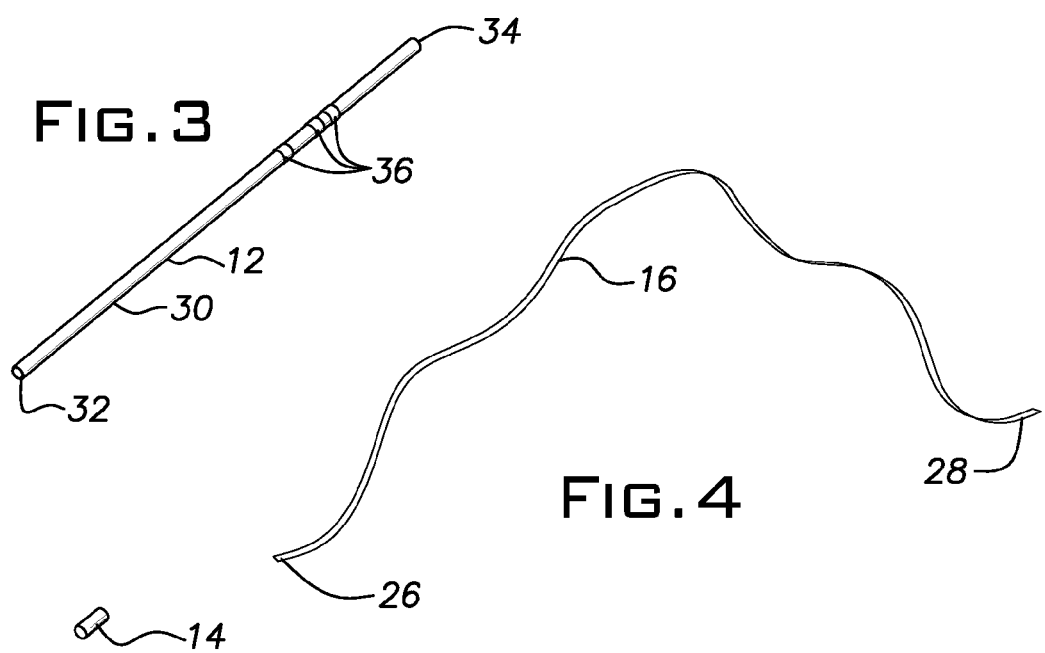

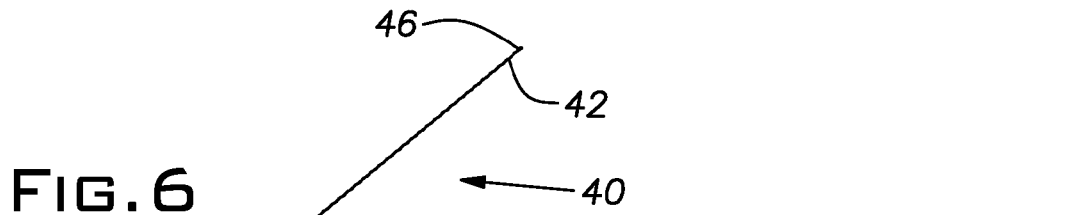
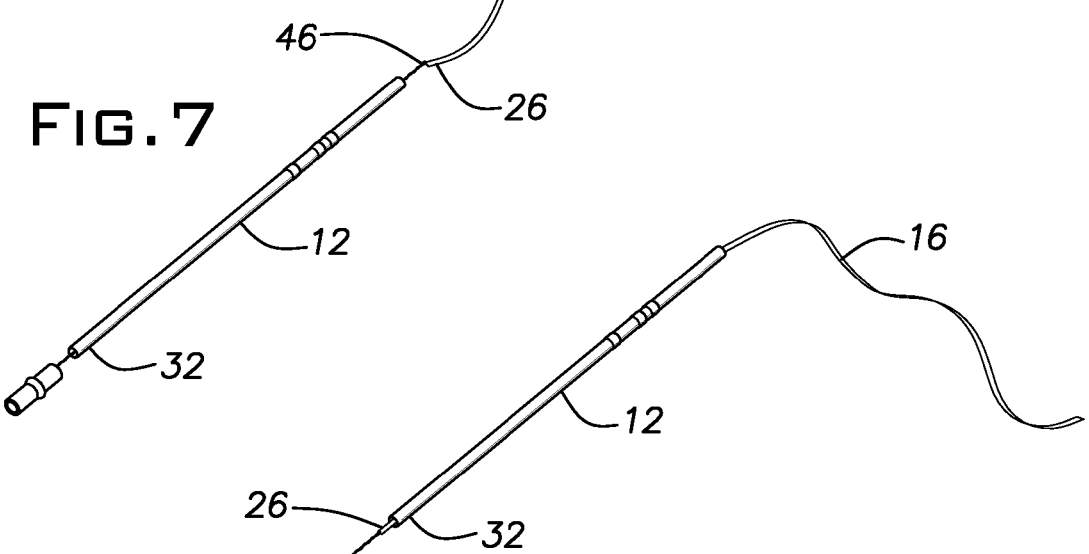
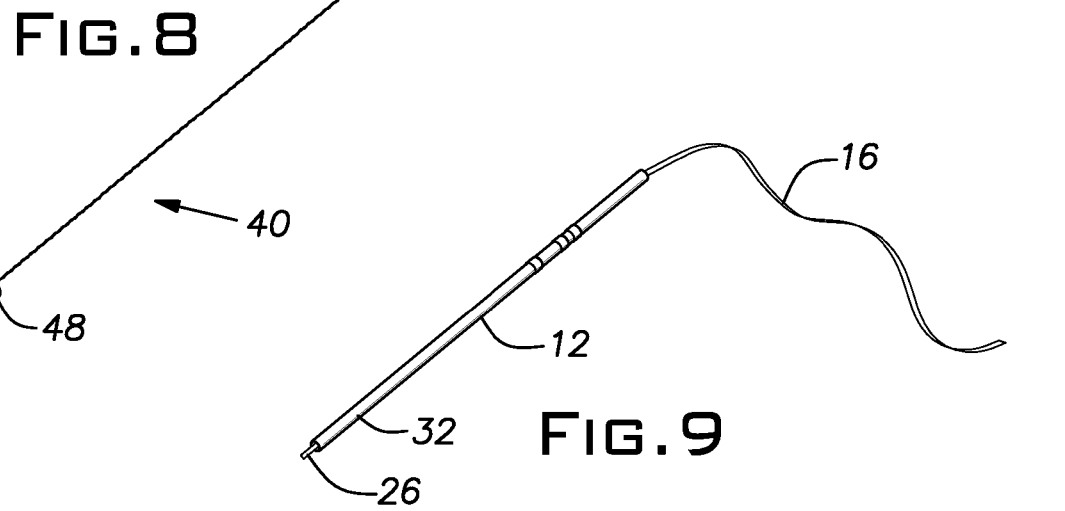

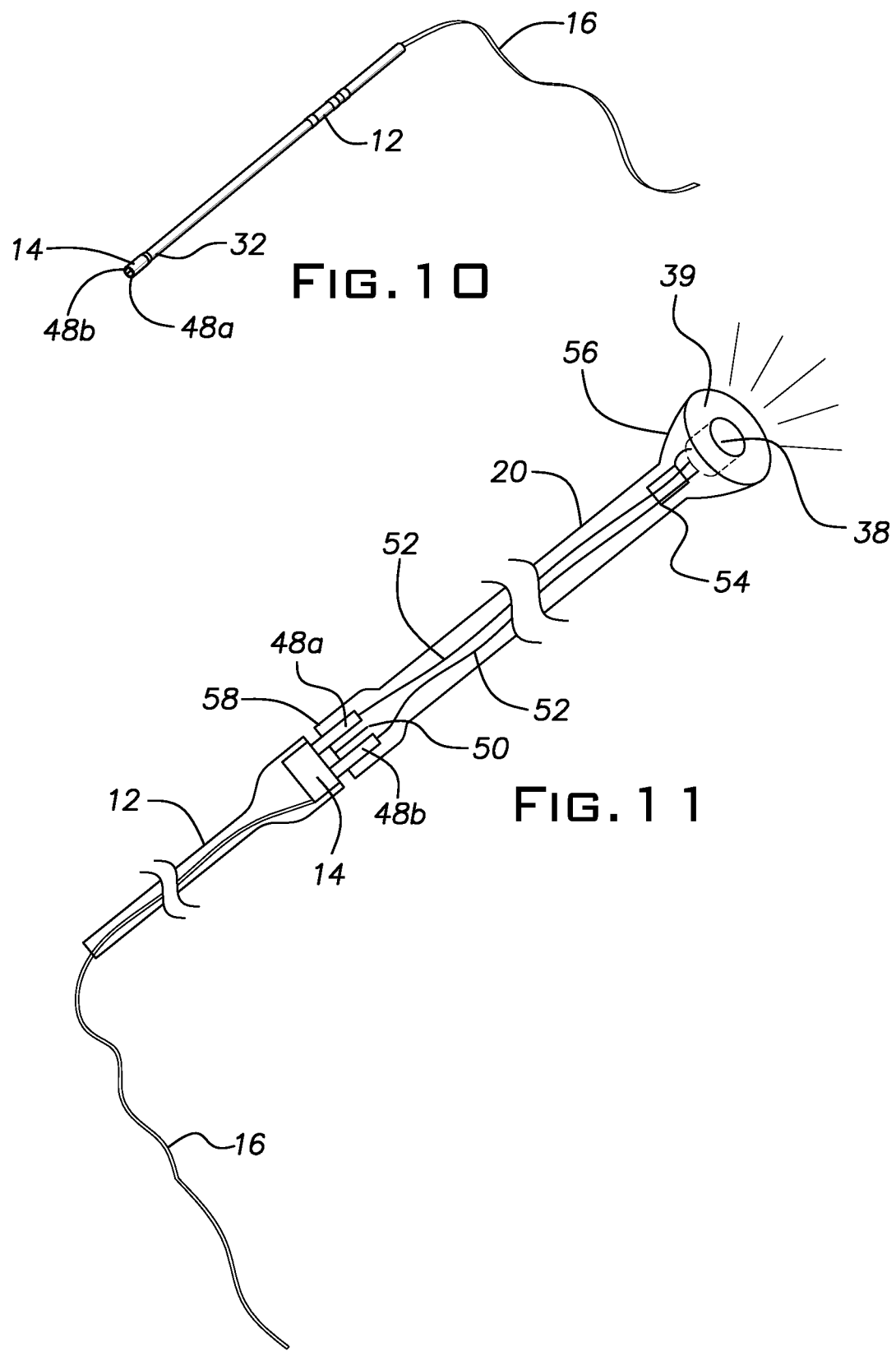

BRIDLE CATHETER WITH ILLUMINATING END

FIELD

The present invention relates to a bridle catheter having an illuminating end for assisting in installing the bridle catheter in a patient and to a method of inserting a bridle catheter into a patient utilizing an illuminating end.

BACKGROUND

In an effort to prevent premature pullouts, nasoenteric tubes are often fixed in place using a wide variety of bridling systems. Prior systems were difficult to place in a patient and presented discomfort, such as the system taught by U.S. Pat. No. 4,778,448 to Meer, where both ends of a bridle are inserted into separate nostrils until the ends are present in the hypopharynx. Each end of the bridle is then extracted through the mouth of the patient using forceps and tied together to form the bridle.

An improvement to this technique is taught by the bridling system of U.S. Pat. No. 6,631,715 to Kim, which uses a flexible tube like member as the bridle for securing a nasal tube. The flexible member has a magnetic end that is inserted into a first nare of the patient's nose and a magnetic probe that is inserted into a second nare of the patient's nose. Both the flexible member and magnetic probe are inserted just beyond the posterior border of the nasal septum. The magnetic probe retrieves the flexible member, which loops the flexible member around the nasal septum. Once the magnetic end of the flexible member is pulled from the second nare and trimmed away, the flexible member remains in the patient and serves as the bridle for retaining a nasal tube, for example.

Another type of bridle system is disclosed in U.S. Pat. No. 5,185,005 to Ballantyne. Ballantyne utilizes two magnetic insertion tools to place a bridle around the posterior nasal septum of the patient. A first insertion tool with the bridle attached is inserted into the first nostril and a second insertion tool is inserted into the second nostril of the patient until they magnetically couple behind the posterior nasal septum. Once coupled, the first insertion tool is removed from the first nostril leaving the bridle coupled to the second insertion tool. The second insertion tool is then removed from the second nostril, which pulls the bridle from the first nostril around the posterior nasal septum and out the second nostril.

In applicant's prior patent, U.S. Pat. No. 7,534,228 to Williams, the disclosure of which is incorporated herein by reference in its entirety, applicant discloses a device that uses a flexible member with a magnet attached to one end of the flexible member and an umbilical tape attached to the flexible member. The flexible member is inserted into a first nare using an insertion tool, which makes the flexible member stiff enough to be inserted into the nasal cavity. A retrieving tool having a magnetic end is inserted into a second nare and couples with the magnet of the flexible member. Once the retrieving tool and the flexible member are coupled magnetically behind the posterior nasal septum of the patient, the retrieving tool is pulled out of the second nare and the flexible member follows around the vomer bone and out the second nare, pulling the umbilical tape with it. The flexible member is pulled entirely out of the second nare, leaving the umbilical tape in position behind the vomer bone.

SUMMARY

An example illuminating bridle installation system and method are disclosed and claimed.

BRIEF DESCRIPTION OF THE DRAWINGS

FIG. 1 is a perspective view of the first example bridle installation system of the present invention in its assembled form;

FIG. 2 is a perspective view of the retrieving member incorporating an illuminating member;

FIG. 3 is a perspective view of the flexible member;

FIG. 4 is a perspective view of the tape portion;

FIG. 5 is a perspective view of the magnet for insertion into the first end of the flexible member;

FIG. 6 is a perspective view of the guide used to thread the tape portion into the flexible member;

FIG. 7 is a perspective view showing the guide inserted into the flexible member, with the tape portion detachably coupled to the first end of the guide;

FIG. 8 is a perspective view showing the guide threading the tape portion through the flexible member;

FIG. 9 is a perspective view showing the tape portion threaded through the flexible member;

FIG. 10 is a perspective view showing the tape portion threaded through the flexible member with a magnet installed in the end of the flexible member;

FIG. 11 is a partial cross-sectional view of the retrieving member coupled to the flexible member showing the example illuminating member;

DETAILED DESCRIPTION

Figure 12:
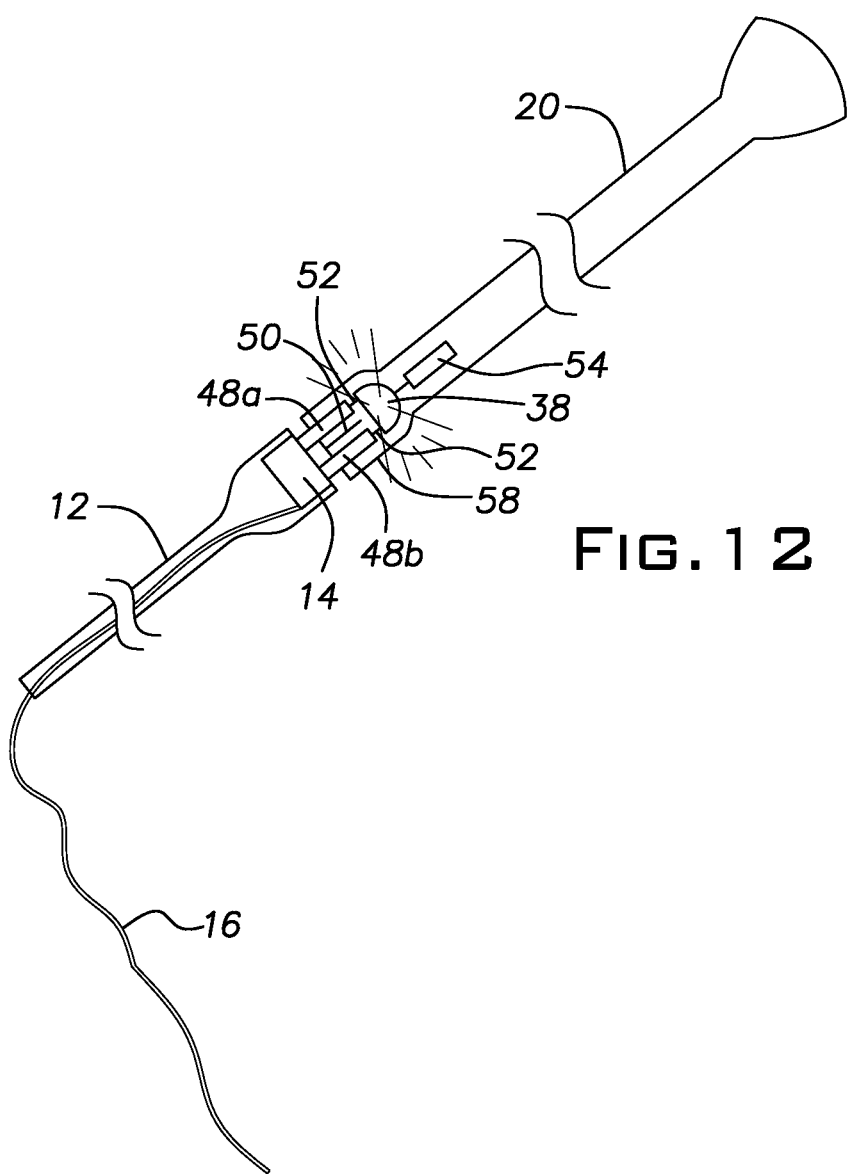
FIG. 12 is a partial cross-sectional view of the retrieving member coupled to the flexible member showing an alternative example illuminating member.
Figure 13:
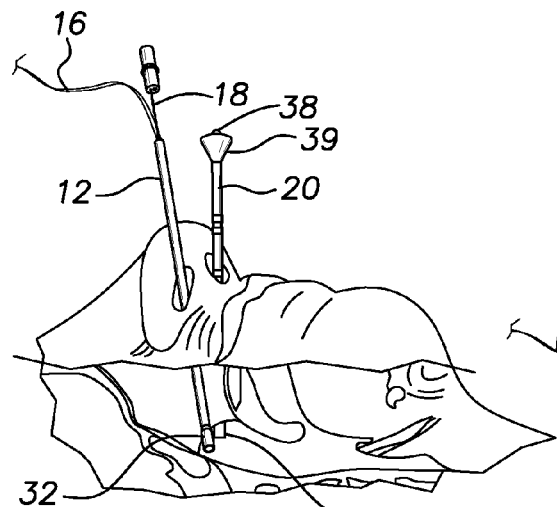
FIG. 13 is a perspective view showing the flexible member and the retrieving member inserted into the patient's nostrils.

In prior methods of installing a bridle in the nasal cavity of a patient, feedback has been used to determine when a first probe couples magnetically with a second probe in the posterior nasal septum of the patient. Such feedback has been in the form of vibrations and/or noise. For example, the magnets may "click" together, and this may be heard by the physician who is installing the bridle. However, in some cases, surrounding noise levels can be high, making it difficult for the physician to hear the "click" when the magnets engage. The example system incorporates a light signal from an illuminating member that occurs when the magnets contact one another, thereby providing positive feedback to the installer. The illuminating element may be positioned at the end of one of the probes so that it can be viewed by the physician when the two magnets engage. When the physician views the light signal, the physician can be assured that the magnets have coupled and then can pull the bridle through the posterior nasal septum in order to install the bridle.

In addition, the sterility of an umbilical tape has been questioned in connection with current bridle installations. The example bridle system discussed herein can incorporate antibiotics and/or antimicrobials in the umbilical tape, as well as a polymer carrier with antibiotics, antimicrobials, and/or bacteriostatic compounds. The umbilical tape may be coated with a hydrophilic coating that makes it slippery when it is wetted. The hydrophilic coating will make it easier to pull the umbilical tape through the nose. Presently, lubricating jelly is applied to the umbilical tape and to the various parts of the system. A hydrophilic coating can also be applied to other components of the system, if desired. The use of the hydrophilic coating can avoid the need to use a lubricating jelly, which can further help to improve sterility as well as convenience. Any known hydrophilic coating may be utilized. While an umbilical tape is discussed in connection with the bridle, other types of members could be utilized to remain in the nasal passage.

Referring now to the drawings, an example illuminating bridle system is depicted. FIG. 1 shows a first embodiment of the bridle catheter 10 in its final assembled state. The bridle catheter 10 includes a flexible member 12, a magnet 14, a tape portion 16, and a rod 18. FIG. 2 shows the retrieving member 20 used to retrieve the flexible member 12 while in the patient's nostril. The retrieving member 20 includes a magnetic first end 22 and a plurality of indicating marks 24. The indicating marks 24 may be used to measure the depth of insertion of the retrieving member 20.

The retrieving member 20 includes a cone-shape or enlarged portion 56 that helps to deter over-insertion of the retrieving tool 20 into a patient's nostril. An illuminating member 38 is coupled to the trailing end 39 of the enlarge portion 56. The enlarged portion 56 can have any shape desired and does not necessarily have to be enlarged.

In FIGS. 3-5, the components of the bridle catheter of FIG. 1 are depicted. The flexible member 12 includes a hollow, flexible tube 30 having a first end 32 and second end 34. The flexible member 12 can be made with any type of flexible material commonly known in the art and chosen with sound engineering judgment. The tube does not necessarily need to be hollow. In the illustrated example, the flexible member 12 is made out of silicone. The flexible member 12 may include a plurality of indicating marks 36 that measure the depth of the flexible member 12 as it is inserted into the patient's nostril. The tape portion 16, shown in FIG. 4, includes a first end 26 and a second end 28. The tape portion 16 can be any type of string-like material suitable for insertion into a patient that is commonly known in the art, such as umbilical tape, although the tape portion could have other configurations that are not tape. The magnet 14 is a powerful rare earth type magnet and is secured in the first end 32 of the flexible member 12 in a known manner. For example, the magnet 32 can be inserted into the open end of the flexible member so that it is trapped by pressure asserted on the magnet by the walls of the flexible member 12. The magnet 14 may alternatively be attached to the flexible in another manner, as long as the magnet 14 cannot be dislodged from the flexible member.

Referring to FIGS. 6-13, assembly of the flexible member 12 with the tape portion 16 is depicted. FIG. 6 shows a guide 40 in the form of a wire 41 having a first end 42 and a second end 44. The first end 42 has an attachment means 46 to attach the first end 26 of the tape portion 16 to the guide 40. The attachment means 46 is used to pull the tape 16 through the hollow interior of the flexible member 12. A handle or knob is attached to the second end 44 of the wire 41 and is used to grasp the guide 40 during the assembly process.

As shown in FIG. 7, the first end 42 of the guide is inserted into the first end 32 of the flexible member 12 until the first end 42 of the guide 40 extends beyond the second end 34 of the flexible member 12. The first end 26 of the tape portion 16 is then attached to attachment means 46 at the first end 42 of the guide 40 and threaded through the flexible member 12, as shown in FIG. 8. The guide 40 is then detached from the first end 26 of the tape portion 16 leaving a small portion of the tape portion 16 extending past the first end 32 of the flexible member 12, as shown in FIG. 9. The magnets 48a, 48b are then installed into the end of the flexible member. Due to the tight fit between the magnets 48a, 48b and the tube of the flexible member, the end 26 of the tape 16 is trapped in the flexible member. Any overhanging tape 16 can be trimmed away, if desired. A flexible member 12 having magnets 48a, 48b installed in the first end 32 thereof is depicted in FIG. 10.

As discussed above in connection with FIG. 2, the example bridle system includes an illuminating member 38, an example of the construction of which is shown in FIG. 11. The illuminating member 38 may be installed in either the retrieving member 20 or in the flexible member 12. The example depicted herein includes the illuminating member 38, which may be an LED light 38, installed in the second or trailing end 39 of the retrieving member 20. By installing the LED 38 in the end 39 of the retrieving member 20, the LED 38 is not required to be pulled through the nasal cavity during the bridle installation process, which allows for a larger LED 38 to be utilized, if desired. FIG. 11 depicts two magnets 48a, 48b installed in the trailing end 39 of the retrieving member 20. The magnets 48a, 48b are separated from one another by a dividing wall 50 or in any known manner. For example, the magnets 48a, 48b could each be coated with an exterior polymer coating so that they cannot touch one another when installed in the end 39 of the retrieving member 20. Each magnet 48a, 48b is coupled to a wire 52 that is positioned inside the retrieving member 20. The wires 52, illuminating member 38, and magnets 48a, 48b of the retrieving member 20 and the magnet 14 of the flexible member 12 together create an electronic circuit (not shown) that has a switch that is normally open. As shown in FIG. 10, when the two magnets 48a, 48b of the retrieving member 20 meet the magnet 14 of the flexible member 12, the magnets 48a, 48b, 14 serve to close the switch of the circuit and the LED illuminating member 38 lights up, indicating to the installer that the magnets 48a, 48b, 14 have coupled together and that the installation of the umbilical tape can be completed. A magnetic switch may be utilized in order to activate the LED illuminating member 38. Other types of switches may be used, as known by those of skill in the art. Any type of device that will allow completion of the circuit may be utilized.

The magnets 48a, 48b, 14 may be any known type of magnets with sufficient strength to allow the magnets to remain coupled during the installation process. Alternatively, a magnet coupled with metallic members could be utilized. For example, the magnets 48a, 48b could couple with a metallic member 14 instead of a magnet 14.

An LED light 38 is discussed above. Other types of lights may alternatively be used, as known by those of skill in the art. A battery 54 may be utilized inside the end of the retrieving member 20 to power the LED light 38. The magnets 48a, 48b, 14 may be attached to the ends of the flexible member 12 and retrieving member 20 in any known manner. In the presently depicted example, the magnets 48*a*, 48*b* are fitted into the end of the hollow tube that forms the retrieving member 20, but could be attached in any known manner. Alternatively, the LED light 38 could be installed in the flexible member 12 in a similar manner and the LED light 38 could then be pulled through the nasal cavity or could be cut off prior to being pulled through, once the light 38 has been illuminated indicating that the magnets 48*a*, 48*b*, 12 of the retrieving member 20 and of the flexible member 12 have coupled.

FIG. 12 depicts an alternative example where the LED light 38 is installed in the insertion end 58 of the retrieving member 20. In this example, the LED light 38 illuminates when the magnets 48*a*, 48*b* meet the magnet 14 of the flexible member in order to close the switch of the electronic circuit. The LED light 38 may be visible through the patient's skin or in the throat of the patient. The LED light 38, in this instance, is small enough so that it can be easily inserted into the nasal cavity. In addition, the LED light 38 must remain cool enough so as to not cause discomfort or harm to the patient. In the example depicted, the LED light 38 is encased in the end 58 of the retrieving member 20 adjacent the two magnets 48*a*, 48*b*. The two magnets 48*a*, 48*b* are coupled to the LED light 38 via wires 52 and a battery 54 is shown installed in the retrieving member 20. The size of each component must be appropriate for installation into the nasal cavity. Other types of lights other than LED lights maybe be utilized. Any known circuit may be utilized for causing the LED light to be illuminated. Any type of switch may be utilized. There may be instances where two magnets are not required and where a single magnet may be utilized, and the claimed example encompasses any such instance.

Figure 14:
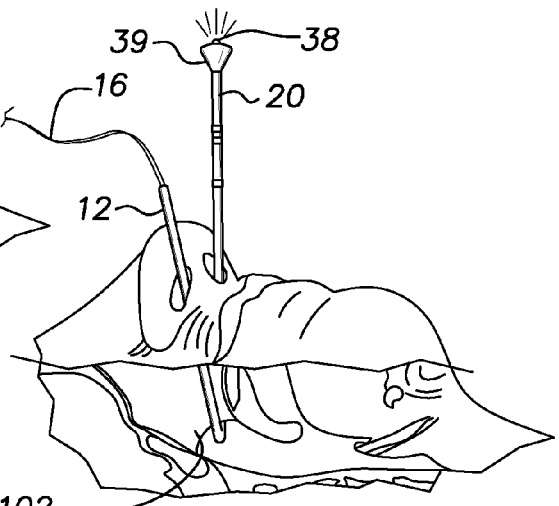
FIG. 14 is a perspective view showing retrieval of the flexible member.
Figure 15:
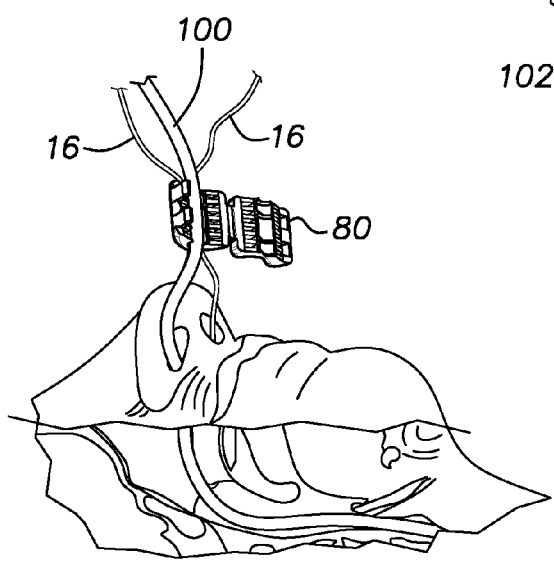
FIG. 15 is a perspective view showing the tape portion installed behind the vomer bone of the patient after the flexible member has been removed, a nasal tube installed in the patient, and the attachment of a clip to secure the tape.
Figure 16:
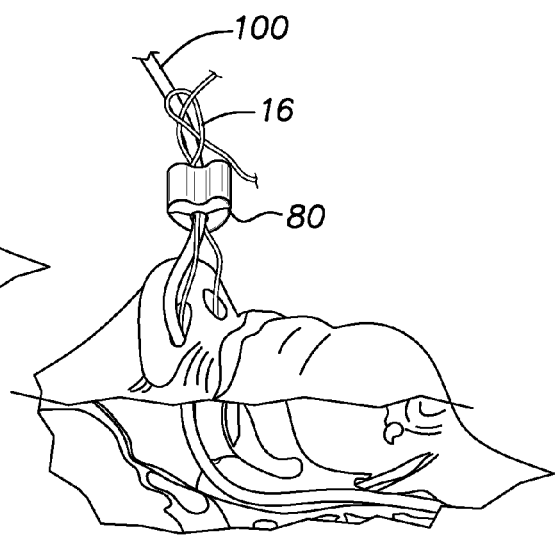
FIG. 16 is a perspective view of the tape portion after placement in the patient and securing the tape portion and nasal tube with a clip.

The bridle catheter may be installed in any known manner FIGS. 13-16 depict an installation process for placing the bridle catheter 10 into a patient. The first end 32 of the flexible member 12 is inserted into the first nostril of the patient and is extended down to the posterior nasopharynx using a stiffening rod 18. The stiffening rod may be initially fully inserted into the flexible member 12, but may be retracted slightly as the flexible member 12 enters the posterior nasopharynx in order to allow the end 32 of the flexible member 12 to bend slightly. The magnetic distal end 22 of the retrieving member 20 is inserted into the second nostril and is also extended down to the posterior nasopharynx. As the retrieving member 20 reaches the posterior nasopharynx, the magnetic distal end 22 attracts the magnet 14 located in the first end 32 of the flexible member 12 causing the magnetic ends to connect or snap together. As shown in FIG. 14, when the magnetic ends connect, the LED 38 on the retrieving member 20 illuminates. This signals to the physician that the magnets have coupled to one another and that the installation may proceed. The rod 18 is then removed from the flexible member 12 and the retrieving member 20 is pulled out of the second nostril, thereby pulling the flexible member 12 through the patient's nose and out the second nostril until only the tape portion 16 remains in the patient. The flexible member 12 is then cut away from the tape portion 16, leaving the tape portion 16 threaded through both nostrils of the patient forming a loop around the vomer bone 102.

After the retrieving member 20 and flexible member 12 are removed from the second nostril, leaving only the tape 16 installed behind the vomer bone, the nasal tube 100 may be installed. The ends of the tape portion 16 and the nasal tube 100 may then be clipped together with a clip 80, such as that shown in FIGS. 14 and 15. The clip 80 may be closed and snapped together. If desired the ends of the tape portion 16 can be tied off for additional security. Any type of clip may be utilized to couple together the ends of the umbilical tape. The clip 80 is shown for example only. Alternatively, a clip is not required and the umbilical tape 16 could be knotted together without a clip or coupled directly to another device.

It should be noted that while the retrieving member 20 is illustrated in FIG. 2 as including only elements 22 and 24, it is contemplated that the retrieving member could also take the form of a second flexible member 12 including elements 14, 36 and a second rod 18. In this embodiment, the retrieving member could be more flexible which may be advantageous especially in pediatric applications.

An illuminating bridle installation system includes a flexible member and a retrieving member. The flexible member has a leading end and a trailing end. At least one first magnet is coupled to the leading end of the flexible member. The retrieving member has a leading end and a trailing end. At least one second magnet is coupled to the leading end of the retrieving member. An illuminating member is coupled to at least one of the leading or trailing end of the flexible member or to the leading or trailing end of the retrieving member. The illuminating member is coupled to one of the at least one first or second magnets and an electronic circuit having a switch that allows the illuminating member to be illuminated when the first magnet meets the second magnet.

The system may also include a tape portion securely coupled to the flexible member. The flexible member may include an antibiotic, bacteriostatic, or antimicrobial coating, a hydrophilic coating, or a combination thereof.

The illuminating member may be an LED light and may further comprise a battery. The illuminating member may be coupled to the trailing end of the retrieving member. The at least one second magnet may comprise two magnets that are installed side-by-side at the leading end of the retrieving member. The two magnets are isolated from one another so that they do not touch one another.

The system may include a rod for insertion into the flexible member to stiffen the flexible member to assist in insertion of the flexible member into a patient.

An alternative example illuminating installation system includes a first probe having at least one first magnet coupled to an end thereof and a second probe having at least one second magnet coupled to an end thereof. An illuminating member is coupled to one of the first and the second probe. An electronic circuit having a switch is coupled to the illuminating member and to the at least one first magnet or to the at least one second magnet. When the at least one first magnet meets the at least one second magnet so as to couple together, the switch of the electronic circuit is closed and the illuminating member is illuminated.

The system may also include a flexible portion coupled to one of the first or the second probes for installation in a nasal cavity of a patient. The illuminating member may be an LED lamp. The at least one second magnet may comprise two magnets that are positioned side-by-side in non-contacting relation at a leading end of the second probe. The illuminating member may be coupled to the second probe at a trailing end of the second probe, with wires extending from the two magnets to the illuminating member.

The first probe may be flexible and may have one magnet coupled to an end thereof. The second probe may be substantially rigid and may have two magnets coupled to an end thereof. The two magnets may be positioned relative to one another so that they do not normally touch. The illuminating member may be coupled to an end of the second probe opposite the end in which the two magnets are installed. The illuminating member may be coupled to the second probe at the end where the two magnets are positioned.

A method of placing a bridle catheter into the nasal cavity of a patient includes providing a flexible member and a retrieving member. The flexible member has a first end and a second end, with a magnet coupled to the first end of the flexible member. The retrieving member has a magnetic first end and a second end having an illuminating member that is operatively coupled to the magnetic first end so as to illuminate when the first end couples with the magnet of the flexible member. The method also includes inserting the first end of the flexible member into a first nostril of a patient and into the posterior nasopharynx, and inserting the first end of the retrieving member into a second nostril of the patient and into the posterior nasopharynx until the illuminating member is illuminated to indicate that the first end of the flexible member is magnetically connected to the first end of the retrieving member. The method also includes pulling the retrieving member and at least part of the flexible member out of the second nostril and cutting the flexible member such that a portion of the flexible member remains in the nasal cavity.

The flexible member may include a first portion and a second portion, with the second portion being a tape portion at the second end thereof. The method may also include pulling the first portion of the flexible member entirely from the second nostril until the tape portion is positioned in the nasal cavity and cutting the first portion from the tape portion so that only the tape portion remains in the nasal cavity.

The method may also include the use of a rod that is inserted into the flexible member for installation of the flexible member into the nostril and posterior nasopharynx. When the illuminating member is illuminated, the rod is removed from the flexible member. In addition, the ends of the flexible member may be secured together. The flexible member may also be coupled to another apparatus.

The examples provided herein are directed toward the installation of a nasal catheter. It should be readily recognized that the examples described herein are equally applicable to other situations where a first member contacts a second member and could find uses in other areas, such as in the airway, GI tract, stomach, or for catheter suture delivery, for example, among other areas of applicability. Alternatively, the example described herein could be utilized in instances where an LED light is illuminated upon contacting a non-magnetic surface.

Other types of bridle systems may also utilize the illuminating member described herein in order to provide positive feedback to the installer. For example, any of the prior art bridle systems that utilize magnets can include an illuminating member such that when the circuit is closed when the magnets engage one another, a light can be illuminated. These other bridle systems are likewise included herein in the example illuminating bridle system and will derive the same benefit from the illuminating member as the above-described bridle system.

As previously discussed, the example bridle system also may incorporate an antibiotic or other coating that can prolong use of the bridle in the nasal cavity. Such antibiotic or other coatings are applied to the umbilical tape prior to installation of the tape in the nasal cavity. Such types of include antibiotic, bacteriostatic, antimicrobial compounds, or combinations thereof, among other known compounds.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. An illuminating bridle installation system comprising:
   a flexible member for installation in a nasal cavity of a patient, the flexible member having a leading end and a trailing end;
   at least one first magnet coupled to the leading end of the flexible member;
   a retrieving member having a leading end and a trailing end;
   at least one second magnet coupled to the leading end of the retrieving member;
   a rod for insertion into the flexible member to stiffen the flexible member to assist in insertion of the flexible member into the nasal cavity of the patient; and
   an illuminating member coupled to at least one of the leading or trailing end of the flexible member or to the leading or trailing end of the retrieving member, said illuminating member being coupled to one of said at least one first or second magnets and an electronic circuit having a switch that allows the illuminating member to be illuminated when the at least one first magnet meets the at least one second magnet,
   wherein the flexible member comprises a hollow tube, and further wherein the rod is for insertion into the hollow tube of the flexible member.

2. The system of claim 1, further comprising a tape portion securely coupled to the flexible member.

3. The system of claim 2, wherein the flexible member includes an antibiotic coating, a bacteriostatic coating, an antimicrobial coating, a hydrophilic coating, or a combination thereof.

4. The system of claim 1, wherein the illuminating member is an LED light and further comprising a battery.

5. An illuminating bridle installation system comprising:
   a flexible member having a leading end and a trailing end;
   at least one first magnet coupled to the leading end of the flexible member;
   a retrieving member having a leading end and a trailing end;
   at least one second magnet coupled to the leading end of the retrieving member, the at least one second magnet comprising two magnets that are installed side-by-side at the leading end of the retrieving member; and
   an illuminating member coupled to the trailing end of the retrieving member, said illuminating member being coupled to one of said at least one first or second magnets and an electronic circuit having a switch that allows the illuminating member to be illuminated when the at least one first magnet meets the at least one second magnet.

6. The system of claim 5, wherein the two magnets are isolated from one another so that they do not touch one another.

7. An illuminating installation system comprising:
- a first probe having at least one first magnet coupled to an end thereof;
- a second probe having at least one second magnet coupled to an end thereof;
- an illuminating member coupled to one of the first and the second probe; and
- an electronic circuit having a switch coupled to the illuminating member and to the at least one first magnet or to the at least one second magnet, wherein when the at least one first magnet meets the at least one second magnet so as to couple together, the switch of the electronic circuit is closed and the illuminating member is illuminated.

8. The system of claim 7, further comprising a flexible portion coupled to one of the first or the second probes for installation in a nasal cavity of a patient.

9. The system of claim 7, wherein the illuminating member is an LED lamp.

10. The system of claim 7, wherein the at least one second magnet comprises two magnets that are positioned side-by-side in non-contacting relation at a leading end of the second probe and the illuminating member is coupled to the second probe at a trailing end of the second probe, with wires extending from the two magnets to the illuminating member.

11. The system of claim 7, wherein the first probe is flexible and has one magnet coupled to an end thereof, and the second probe is substantially rigid, and has two magnets coupled to an end thereof, with the two magnets being positioned relative to one another so that they do not normally touch.

12. The system of claim 11, wherein the illuminating member is coupled to an end of the second probe opposite the end in which the two magnets are installed.

13. The system of claim 11, wherein the illuminating member is coupled to the second probe at the end where the two magnets are positioned.

14. A method of placing a bridle catheter into the nasal cavity of a patient comprising:
- providing a flexible member having a first end and a second end, with a magnet coupled to the first end of the flexible member;
- providing a retrieving member having a magnetic first end and a second end, with an illuminating member that is operatively coupled to one of the magnetic first end or the second end so as to illuminate when the first end couples with the magnet of the flexible member;
- inserting the first end of the flexible member into a first nostril of a patient and into the posterior nasopharynx;
- inserting the first end of the retrieving member into a second nostril of the patient and into the posterior nasopharynx until the illuminating member is illuminated to indicate that the first end of the flexible member is magnetically connected to the first end of the retrieving member;
- pulling the retrieving member and at least part of the flexible member out of the second nostril; and
- cutting the flexible member such that a portion of the flexible member remains in the nasal cavity.

15. The method of claim 14, wherein the flexible member includes a first portion and a second portion, with the second portion being a tape portion at the second end thereof and further comprising:
- pulling the first portion of the flexible member entirely from the second nostril until the tape portion is positioned in the nasal cavity and cutting the first portion from the tape portion so that only the tape portion remains in the nasal cavity.

16. The method of claim 14, wherein a rod is inserted into the flexible member for installation of the flexible member into the nostril and posterior nasopharynx and when the illuminating member is illuminated, further comprising removing the rod from the flexible member.

17. The method of claim 14, further comprising securing the ends of the flexible member together.

18. The method of claim 17, further comprising coupling the flexible member to another apparatus.

* * * * *